United States Patent [19]

Kellett

[11] Patent Number: 5,063,782
[45] Date of Patent: Nov. 12, 1991

[54] ACCELEROMETERS AND ASSOCIATED CONTROL CIRCUITS

[76] Inventor: Michael A. Kellett, 177 York Rd., Stevenage, Hertfordshire, United Kingdom, SG1 4HA

[21] Appl. No.: 438,411
[22] PCT Filed: Jun. 20, 1988
[86] PCT No.: PCT/GB88/00474
§ 371 Date: Dec. 15, 1989
§ 102(e) Date: Dec. 15, 1989
[87] PCT Pub. No.: WO88/10431
PCT Pub. Date: Dec. 29, 1988

[30] Foreign Application Priority Data

Jun. 18, 1987 [GB] United Kingdom ............... 8714274
Jun. 18, 1987 [GB] United Kingdom ............... 8714275

[51] Int. Cl.$^5$ ............................................. G01P 11/08
[52] U.S. Cl. ..................................... 73/654; 310/329; 73/517 R
[58] Field of Search ................. 73/654, 35, DIG. 4; 310/329, 319

[56] References Cited

U.S. PATENT DOCUMENTS

| | | | |
|---|---|---|---|
| 3,940,974 | 3/1976 | Taylor | 73/DIG. 4 |
| 4,374,472 | 2/1983 | Nishimura | 73/35 |
| 4,473,768 | 9/1984 | Kerr et al. | 310/329 |
| 4,658,650 | 4/1987 | Yorinaga et al. | 73/654 |

Primary Examiner—John E. Chapman
Attorney, Agent, or Firm—Locke Reynolds

[57] ABSTRACT

An accelerometer unit characterized by first and second piezo-electric elements (5, 6) mounted upon opposed surfaces of an electrically conductive sheet, plate or the like (1), and in that the sheet, plate or the like is adapted to be centrally supportable by support (12) such that the first and second piezo-electric elements are subjectable to similar forces upon subjecting the piezo-electric elements to acceleration forces. The elements (5, 6) are connected electrically in parallel so that the effects of one piezo-electric element are caused to negate electrical output arising from pyroelectric effects of the other piezeo-electric element. A combined band pass filter and amplification circuit in which at least a part of the capacitance (37) of the initial high frequency pass filter of the circuit is provided by the capacitance of the piezo-electric elements.

9 Claims, 3 Drawing Sheets

ACCELEROMETERS AND ASSOCIATED CONTROL CIRCUITS

This invention relates to low frequency accelerometers, and associated control circuits, and in particular to piezoelectric low frequency accelerometers and their associated filter and amplifier circuits.

In many applications it is important in the construction of piezoelectric accelerometers to keep production costs as low as possible while at the same time endeavoring to attain as high as possible electrical output in relation to the acceleration induced into the piezolelectric elements involved.

In practice in relation to the construction of piezoelectric accelerometers for use at low frequencies it is also necessary to maximize the source capacity since it has been found that the provision of high source capacitance facilitates simplification of the design of systems, installations or the like in which such accelerometer are utilized.

In known arrangements for the production of acceptable accelerometers using piezoelectric material in the so-called radial mode of strain application, the piezoelectric material is subjected to compressive or tensile forces along directions radially directed of the mounting thereof from a support.

With such known arrangements it is a common practice, to deposit a layer of piezoelectric material onto a support element of the requisite mechanical properties. This support element can, if desired, be formed by a further piezo electric material.

To maximize the sensitivity of the device it is conventional practice to arrange for the line of zero strain of the resulting accelerometer to lie along the junction between the piezoelectric element(s) and the associated support.

It is convenient to note that, in general, piezoelectric materials are operationally reversible in that an applied mechanical strain will produce an electrical output and in that any electrical signal input will produce a related mechanical strain effect in the piezoelectric material. In addition, piezoelectric materials are pyroelectric since any change in the temperature of the piezoelectric material will produce a corresponding electrical output.

In this connection it has been found that relatively small changes in the ambient temperature cause production of electrical outputs related to the temperature change and which are sufficiently large enough to cause spurious readings from the accelerometer.

It is an object of the present invention to provide an accelerometer which is particularly suitable for use at low frequencies, and in which the significance of ambient temperature changes upon the output of an accelerometer is reduced.

The frequency range for accelerometer applications contemplated for the present invention is from 0.1 Hz to 500 Hz. Within this range it is desirable that the lower limit should be selectively variable at least within the range 0.1 Hz to 20 Hz. In the case of the upper range limit such selective adjustment should be at least possible between 10 Hz and 500 Hz. Also it is required that the source impedance should be less than 1000 Ohms, and that any associated circuitry should be able rapidly to recover from overloads of up to, for example, in applications of accelerometers to the monitoring of the performance of a motor vehicle suspension system, 3 g for accelerometers mounted to the body of a vehicle and up to 50 g in applications where the accelerometers are mounted to the wheels of a vehicle. In so far as the question of ambient temperature conditions is concerned the accelerometer needs to be capable of operating over a temperature range of −55 to +125 degrees Celsius.

A further object of the invention is to provide an accelerometer in which the effects of the inherent pyroelectric characteristics of the piezo electric material are eliminated or are at least reduced. It is a still further object of the present invention to provide a band pass filtering and amplifying circuit which is able to operate with a low voltage supply of, for example, 5 volts, which is suitable for use with low frequency piezo electric accelerometers and which is able to produce from the output of the accelerometer a high level low impedance signal for subsequent processing and/or use.

It is a common practice to use a combined filtering and amplifying circuit with accelerometers and it has been found that there are two severe problems associated with piezoelectric accelerometers which lead to serious difficulties in the design of filtering and amplifier circuits. The first arises as a result of the inherent pyroelectric response of piezoelectric materials to changes in temperature which creates spurious output signals. This output is an amount of electrical charge per degree of temperature change. In practice, if a resistive load is connected across a piezoelectric element then the maximum voltage produced across any such load due to pyroelectric effect will be proportional to the rate of change of the temperature and inversely proportional to the magnitude of the resistive load. The minimum value for the resistive load is determined by the lower limit of the frequency response required. The pyroelectric effect output signal may be reduced by lengthening the thermal time constant of the accelerometer system and by using high frequency pass filters to prevent the low frequency pyroelectric noise signals from appearing at the output of the accelerometer system. In a practical arrangement the pyroelectric signals are so large as compared with the desired signal output of the accelerometer, i.e., that due to an acceleration variation, that no amplification of the signal can be allowed in advance of an initial high pass filtering, so as to avoid any amplification stage from being over-loaded by the low frequency pyroelectric signals. Furthermore, this problem is aggrevated by the use of a low power supply voltage.

The second problem is concerned with preventing signals at frequencies above the required pass band frequency range from appearing at the output of the system. The difficulties arising from the fact that the piezoelectric accelerometer will exhibit resonant behavior at frequencies determined by the precise method of mounting and by the geometry and properties of the various materials employed in the construction of the accelerometer. This situation causes an increase in the sensitivity of the accelerometer at higher frequencies which need to be eliminated by a complementary reduction in the gain of an associated amplifier and filter circuit. In a practical accelerometer an increase of sensitivity by a factor of 20 is possible at frequencies as low as 2 kHz compared with the sensitivity at 20 Hz. This situation requires that the low band pass section of the circuit should precede any amplification stage.

According to a first aspect of the invention there is provided an accelerometer unit including first and second piezoelectric elements mounted upon opposed surfaces of an electrically conductive sheet, plate or the like adapted to be centrally supportable such that the first and second piezoelectric elements are subjectable to similar forces upon subjecting the piezoelectric elements to acceleration forces, and characterised in that the first and second piezoelectric elements are connected electrically in parallel whereby any electrical output arising from pyroelectric effects of one piezoelectric element are caused to negate electrical output arising from pyroelectric effects of the other piezoelectric element.

Preferably said first and second piezoelectric elements are of annular form and are arranged co-axially of the support, the sheet, plate or the like and the support means each having a through bore, and in that an electrical connection to the outermost piezoelectric element of the first and second piezoelectric elements passes through both elements, the sheet, plate or the like and the support.

Preferably, the first and second piezoelectric elements are so secured to the sheet, plate or the like as to provide an integral composite element.

Conveniently the piezoelectric elements are secured the sheet plate or the like by adhesive.

Conveniently, there is provided in connection with the accelerometer unit a combined band pass filter and amplification unit in which the source capacitance of the accelerometer unit is utilized as at least a part of the capacitance of the initial high frequency level pass filter of the circuit.

Preferably, the source capacitance provides the total capacitance for the filter.

For a better understanding of the invention and to show how to carry the same into effect reference will now be made to the accompanying drawings in which.

Figure 1:
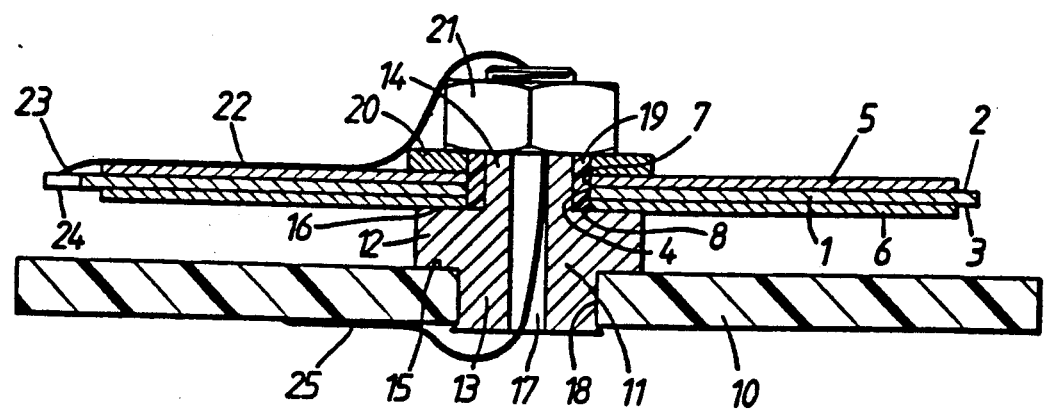
FIG. 1 is a view in section of an accelerometer incorporating the principles of the invention.
Figure 2:
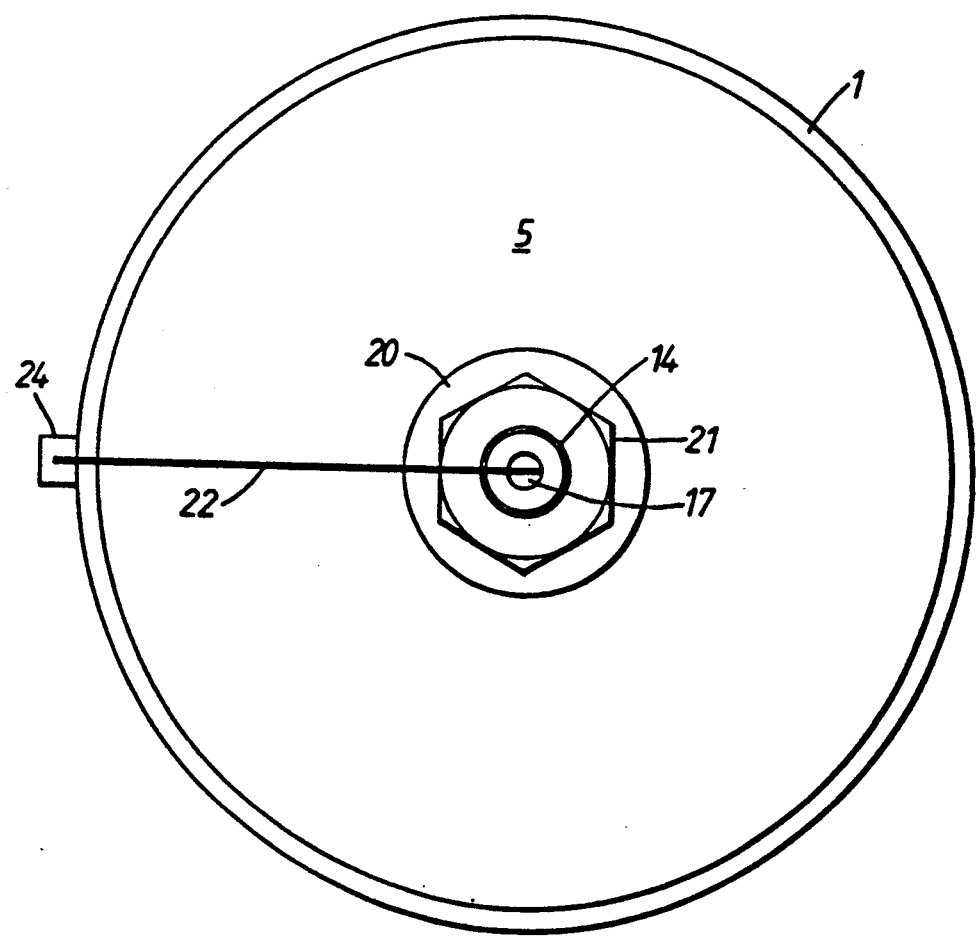
FIG. 2 is an elevation of FIG. 1.

Referring to FIG. 1 an annular support element 1 has annular surfaces 2 and 3 and a central bore 4. First and second disc-like annular piezoelectric elements 5 and 6 having the same external diameter of, for example, 20–40 millimeters are respectively bonded to or deposited upon the surfaces 2 and 3. The elements 5 and 6 have central bores 7 and 8 respectively and are so positioned upon the support that these bores 7 and 8 are co-axial with the bore 4 of the support 1.

The sandwich comprising the support 1 and the two piezoelectric elements is supported from a main support plate or the like 10 by way of an electrically conductive post 11, including a main body 12, a first smaller diameter portion 13 and a second smaller diameter portion 14. The provision of the two smaller diameter portions 13 and 14 leads to the provision of annular abutment surfaces 15 and 16 respectively at the opposite ends of the main body 12. The post 11 has an axial through bore 17.

The smaller diameter portion 13 engages in a through bore 18 in the main support plate 10. To ensure that the post is firmly connected to the plate 10 the free end region of the portion 13 is swaged so as to overlie the adjacent edge portion of the rim of the bore 18 thereby cramping the plate 10 between the swaged part and the abutment surface 15 thereby firmly connecting the post 11 to the plate 10.

An electrically insulating sleeve 19 is engaged over the smaller diameter portion 14. The outer diameter of the sleeve 19 is such that it is a clearance fit into the bores 7 and 8 of the piezoelectric elements 5 and 6 and the bore 4 of the support 1.

In addition, it will be noted that the inner peripheral region of the outermost surface of the element 6 is in electrical contact with the main body 12 of the post 11.

An electrically conductive washer 20 is engaged over the portion 14 to overlie the inner peripheral region of the outermost surface of the piezoelectric element 5 and makes electrical contact therewith.

The assembly of the washer and sandwich on the post is held in place by a nut 21 engaging with a threaded part of the portion 14.

It should be noted that the thickness of the washer 20 is chosen such that the outermost annular surface thereof is sufficiently above the outermost annular surface of the sleeve 19 as to ensure that, when the nut 21 is tightened, electrical contact is ensured between the piezoelectric element 5, the washer 20, the nut 21, and the post 11 and thus between the outermost surfaces of both of the piezoelectric elements 5 and 6.

Electrical connection is automatically made between the internal faces (those adjacent to the surfaces 2 and 3 of the support 1) of the piezoelectric elements 5 and 6 since the support 1 is itself electrically conductive. Hence the internal faces thereof are effectively connected electrically in parallel to each other. The support 1 is electrically coupled to a desired location of the main support 10 by a wire 22 which at one end 23 is connected to the support 1 by way of a connection tag 24 provided on the periphery of the support 1 and whose other end 25 connects with the main support 10.

For convenience, the wire 22 passes to the underside of the support 10 by way of the central bore 17 in the post 11 so that the other end 25 of the wire 22 can be connected to a desired loction of the support 10. It will be appreciated that the location of connection of the wire end 25 to the support 10 will be electrically isolated from the swaged over parts of the post portion 13. To offset unacceptable vibration of the wire 22, the latter can be bonded to the adjacent element 5 intermediate of the attachment to the tag 24 and the engagement of the wire with the post.

In practice, the support 10 is constituted by a printed circuit board. With this arrangement it will be appreciated that the post 11 can be effectively regarded as an electrical component so that on mounting the post the latter will automatically connect with the correct part of any printed circuit provided upon the board.

The two piezo electric elements 5 and 6 can be mounted to the support 1 in such manner as to form an integral composite unit. Conveniently, the two elements 5 and 6 are attached to the support by adhesive. Furthermore, the connection lead to the piezoelectric elements can be secured by adhesive to the surface of the associated element.

In use, if the accelerometer constuction is accelerated longitudinally of the post 11 the required force being applied to the accelerometer by way of the support 10 then, the inertia of the periphery of the sandwich comprising the support 1 and the piezoelectric elements 5 and 6 will cause strain to be produced in the two piezoelectric elements 5 and 6 of a magnitude proportional to the acceleration, thereby producing an electrical output signal which is proportional to the applied acceleration.

It will be appreciated that with the above described accelerometer the pyroelectric outputs of the two piezoelectric elements 5 and 6 will cancel each other.

With the above construction it has been found that with a combined source capacity (piezo electric elements capacitance) of substantially 50 nF the accelerometer has an output of 30 millivolts/g.

In addition, it will be noted that the construction of the accelerometer of the invention has the added advantage that the source capacity of the parallel connected piezoelectric elements is effectively increased by a factor of four as compared with the source capacity of a conventional bimorph piezoelectric element of the same physical dimensions as either of those included in the accelerometer of the invention.

A particular application of the described accelerometers is to the measurement of motor vehicle wheel and body acceleration with a view to providing information upon the instantaneous conditions prevailing in the suspension system of the vehicle which information can be used as input to a control system for enabling adjustment of the operational characteristics of the suspension system with a view to at least enhancing passenger comforts.

Figure 3:
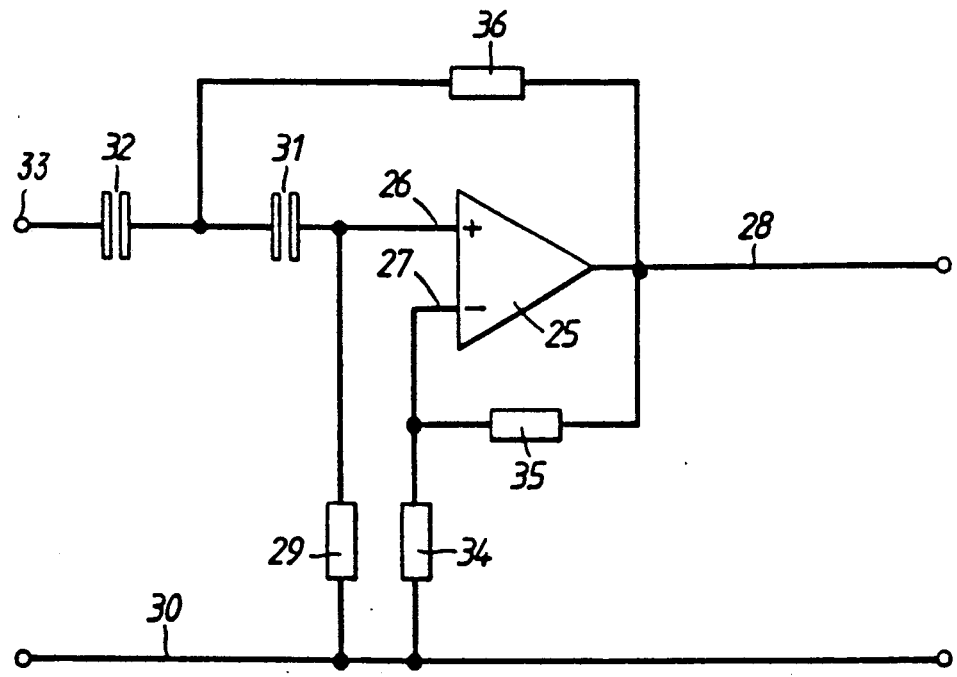
FIG. 3 illustrates a known filter and amplifier circuit.

Referring to FIG. 3 which illustrates a high frequency pass filter circuit known as a Salen and Key Filter. The circuit essentially incorporates an amplifier stage including an amplifier 25 having positive and negative voltage inputs 26 and 27 and an output 28. The input 26 is connected by way of a resistor 29 to a common ground line 30, and by way of serially coupled capacitors 31 and 32 to the signal input terminal 33 of the circuit.

The negative input 27 of the amplifier connects with the line 30 by way of a resistor 34. The output 28 is connected through a resistor 35 to the input 27 and thus effectively in series with the resistor 34, and by way of a further resistor 36 to the junction of the capacitors 31 and 32. The amplifier output 28 provides the output of the filter and amplifier circuit.

In use, the capacitors 31 and 32 and the resistors 29 and 36 serve as the high pass filter for the circuit while the combination of the resistances 35 and 36 control the pass band gain of the complete circuit.

The circuit of FIG. 3 has certain inherent deficencies, when used as a high pass filtering and amplifier circuit for use with piezoelectric transducers as a result of the consequences of piezoelectric material being pyroelectric and also exhibiting a non-linear frequency response leading to greater sensitivity at higher frequencies.

Figure 4:
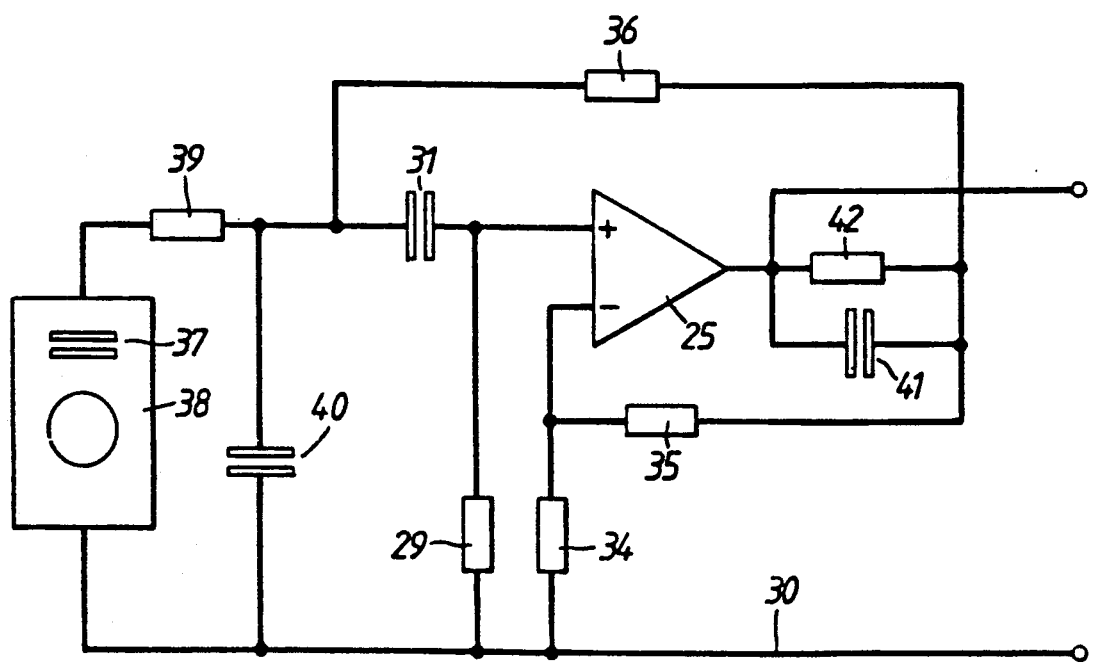
FIG. 4 illustrates an embodiment of a filter and amplification circuit in accordance with the invention.

In accordance with the present invention, the input high pass filter is modified by incorporating as at least a part of the high pass filter the actual capacity of the piezoelectric transducer. This is shown in FIG. 4 in which the capacitor 32 of FIG. 3 is replaced by the source capacitance 37 of the piezoelectric transducer 38. In addition, with a view to controlling (irrespective of any voltage gain at the amplifier stage) the magnitude of any high frequency input to the amplifier below a level at which input signals would be clipped, a low pass input filter is introduced into the circuit. This low pass filter includes the resistor 39 and the shunt capacitor 40.

The significance of the modifications to the basic circuit may be briefly considered as follows:

The introduction of the transducer source capacity as part of the initial high pass filter of the circuit facilitates close control over the level of the low frequency cut-off frequency of the circuit and any phase shifts involved.

With the introduction of the shunt capacitor 40 and the series resistor 39, it is necessary to ensure that the impedance of the piezoelectric transducer capacity is much greater than that of the resistor 39 so that the introduction of the latter will not adversely affect the effectiveness on the high pass frequency performance of the overall circuit. However, the low pass filter combination of the resistance 39 and the capacitor 40 is effective in reducing the overall circuit gain at the higher frequncies.

In practice, provided that the high frequency cut-off level is set to be at least a factor of fifty times the frequency of the low pass filter cut-off frequency corner, any interaction between the two filters will not affect the performance of the high pass filter to any significant extent.

It is convenient to note that the capacitor 40, in so far as the high pass filter is concerned, is effectively coupled in parallel with the piezo electric transducer source capacity 37. This has the additional effect of causing a reduction in the output voltage of the circuit of FIG. 4. In practical terms, this reduction can be reduced as far as possible by selecting the value of the capacitor 40 to be much less than that of the transducer source capacitance.

In practice, the Q of the filter circuit is determined by the ratio of the values of the resistors 34 and 35, which additionally determine the band pass gain of the filter circuit.

If required, it is possible to increase the band pass gain of the circuit and at the same time introduce a second low pass section to the filter circuit. This is achieved by introducing the capacitor 41 and the resistor 42 at the output side of the amplifier 25.

As so far discussed the circuit of FIG. 4 has been found to provide a satisfactory performance in the filtering of the output from the piezoelectric transducer 38 and in controlling the effects of peak voltages arising from, for example, overload conditions and which are in excess of supply voltage levels.

However, for certain applications of accelerometers, for instance, their application to the control of suspension systems of motor vehicles, the rate of recovery from large overloads which have created excessive peak voltage level signals lying within acceptable frequency bands for the filter circuit may well be regarded as being too slow for such an application for the accelerometers.

Figure 5:
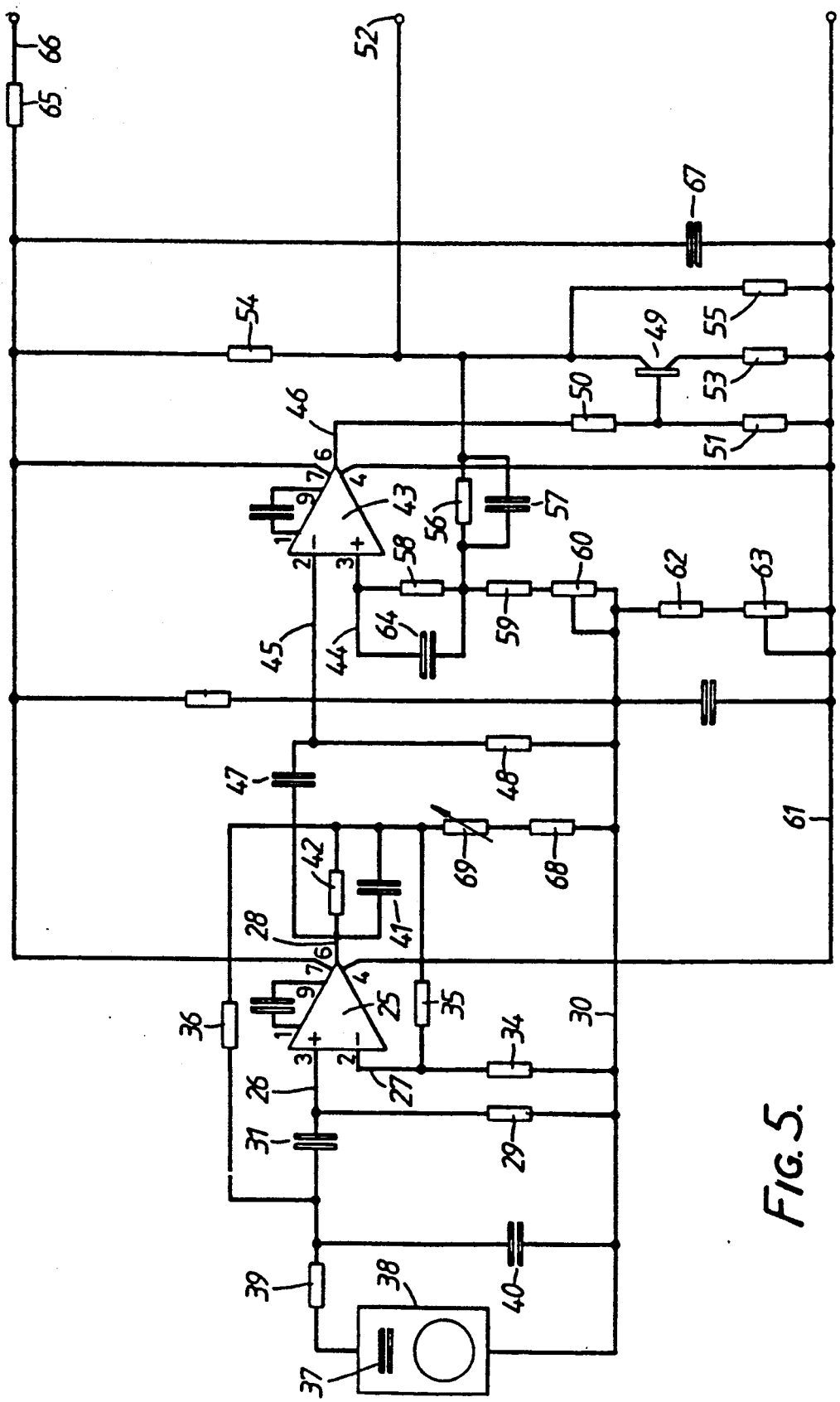
FIG. 5 is a circuit diagram of a more detailed version of the circuit of FIG. 4.

In order to control this overload situation it is necessary to restrict the overall gain of the circuit thereby to prevent overload conditions from arising during normal conditions of use of a transducer. To deal with this particular problem it is proposed to provide the circuit of FIG. 4 with an additional amplification stage, thereby to enable the requisite extra gain for the circuit, together with further band pass filtering and output buffering. FIG. 5 is a circuit diagram of a circuit incorporating the circuit of FIG. 4 together with the additional stages mentioned above.

The circuit of FIG. 5 incorporates a second amplifier 43 with inputs 44, and 45 and an output 46. The output 28 of the first amplifier 25 is coupled to the input 45 of the second amplifier 43 by way of a capacitor 47 which in conjunction with a resistor 48 provides a further high pass filter.

It will be noted that apart from the capacitor 47 the second amplification stage is direct coupled to the output 28 of the first amplifier in order that the second amplification stage will exhibit the required fast overload recovery capability required from the overall circuit.

As a result of the particular amplifiers used (units known under the reference identification LM208) input protection diodes are provided, which diodes are arranged to conduct if the differential input voltage exceeds approximately 0.5 volts. If the output should be large enough to cause this conduction of the input protection diodes the capacitor 47 will charge or discharge whereafter a relatively long time period will be required for their output to reach equilibrium after an input signal is removed. Thus the gain of the first amplification stage must be set so that the peak AC signal at the output 28 from the first amplifiction stage cannot exceed 0.5 volts for any normal input signals to the circuit.

The output 46 of the second amplifier 43 is buffered and inverted by an NPN transistor 49 with a view to obtaining a larger output voltage swing than can be attained from an amplifier. Resistors 50 and 51 are provided in the transistor base circuit to ensure that the output voltage of the second amplifier 43 is about 2.5 volts for an output voltage of 2.5 volts at an output terminal 52. The gain of the transistor stage is controlled by the resistors 53 and 54. These resistors also determine the lowest output voltage that can be obtained. A typical ratio is 1:20.

A resistor 55 is included to limit the maximum output voltage to a value slightly below that of the input power supply in order that any associated control circuitry involved can distinguish the difference between a large signal and a partially disconnected transducer.

A resistor 56 provides negative feedback while the combination of this resistor 56 and a capacitor 57 in parallel therewith provides a further stage of low pass filtering.

The input 44 of the amplifier 43 connects by way of resistors 58, 59, and a variable resistance 60 to the voltage line 30, the latter being connected to a common ground line 61 by way of a resistor 62 and a second variable resistor 63.

In practice, the ratio of the values of the resistor 59 and the variable resistor 60 to the value of resistor 56 determines the gain of the second amplifier stage. As mentioned above the second amplifier stage is DC coupled to allow for the required fast overload recovery. This condition imposes the requirement that the source resistances to the two amplifiers 25 and 43 need to be balanced to reduce any errors caused by input bias currents.

In the further filter arrangement including the resistor 48 and the capacitor 47, the value of the resistor 48 is of necessity of a large value to reduce the capacitance of capacitor 47, a value of 10 Megohms being typical. The resistor 59 has to be of a value much less than that of resistor 48 whereupon the resistor 58 is required as a DC balance resistance. The resistor 58 is shunted by a capacitor 64 to prevent the introduction of unwanted phase shifts at the input 44 to the second amplifier 43 due to its input capacity acting with the resistor 58.

The variable resistor 63 is provided to adjust for the 2.5 volts bias voltage required on the voltage line 30 and to enable fine adjustment of DC offset at the circuit output 52.

A high frequency filter incorporating a resistor 65 provided in the positive voltage supply line 66 and a capacitor 67 connecting the supply line 66 to the common line 61 is provided to remove any high frequency noise components which may be present on the 5 volts supply line.

To provide for compensation for a fall in the output of the transducer as a result of an increase in the temperature of the transducer a negative temperature coefficient thermistor 68 and an associated load resistor 69 are provided between the voltage line 30 and the filter circuit 41,42.

I claim:
1. An accelerometer unit comprising:
an electrically conductive plate having a center portion including an opening therethrough and an edge portion,
first and second piezoelectric elements of substantially identical configuration mounted on opposite surfaces of the electrically conductive plate including openings concentric with the opening in the electrically conductive plate,
a post having a longitudinal bore, the post being received through the openings in the piezoelectric elements and electrically conductive plate for supporting the center portion of the plate, the edge portion being free to flex in response to applied acceleration forces, an electrically insulative sleeve being disposed in said openings in the piezoelectric elements and electrically conductive plate and surrounding said post, and
means connecting the first and second piezoelectric elements electrically in parallel for offsetting any electrical signals arising from pyroelectric effects of the piezoelectric elements.

2. An accelerometer unit as claimed in claim 1 wherein the means for offsetting the electrical outputs arising from pyroelectric effects of the piezoelectric elements includes an electrical conductor connected to said edge portion of the electrically conductive plate and passing through the longitudinal bore in the post.

3. An accelerometer unit comprising:
an electrically conductive plate having a center portion including an opening therethrough and an edge portion,
first and second piezoelectric elements of substantially identical configuration mounted on opposite surfaces of the electrically conductive plate including openings concentric with the opening in the electrically conductive plate, wherein each of the piezoelectric elements includes an outside surface facing away from the electrically conductive plate,
a post having a longitudinal bore, the post being received through the openings in the piezoelectric elements and electrically conductive plate for supporting the center portion of the plate, the edge portion being free to flex in response to applied acceleration forces, and
means connecting the first and second piezoelectric elements electrically in parallel for offsetting any electrical signals arising from pyroelectric effects of the piezoelectric elements, wherein the means for offsetting the electrical outputs arising from pyroelectric effects of the piezoelectric elements further includes means for electrically connecting the outside surfaces of the piezoelectric elements to said post.

4. An accelerometer unit comprising:

an electrically conductive plate having a center portion and an edge portion, the center portion including an opening therethrough, first and second piezoelectric elements mounted on opposite surfaces of the electrically conductive plate, the first and second piezoelectric elements including openings concentric with the opening in the electrically conductive plate, a post having a longitudinal bore, the post being received through the openings in the piezoelectric elements and electrically conductive plate for supporting the center portion of the plate, the edge portion being free to flex in response to applied acceleration forces, an electrically insulative sleeve disposed in said openings in the piezoelectric elements and electrically conductive plate and surrounding said post, connecting means connecting the first and second piezoelectric elements electrically in parallel to a pair of electrodes, the piezoelectric elements exhibiting an inherent capacitance of known value, the piezoelectric elements generating an electrical signal across the electrodes which is proportional to the acceleration experienced by the piezoelectric elements, and an amplification circuit for amplifying the electrical signal generated by the piezoelectric elements, the amplification circuit including at an input thereof a resistor coupled to a first of the electrodes to define with said inherent capacitance a pass filter for restricting the frequency of the signal generated by the piezoelectric elements which the amplification circuit will amplify.

5. An accelerometer unit as claimed in claim 4 wherein the connecting means comprises an electrical conductor connected to said edge portion of the electrically conductive plate and passing through the longitudinal bore in the post.

6. An accelerometer unit as claimed in claim 5 wherein the connecting means further comprises means for electrically connecting outside surfaces of the piezoelectric elements to said post.

7. The accelerometer unit of claim 6 further comprising thermistor means for compensating for any change in the electrical signal due to a change in the operational temperature of the piezoelectric elements.

8. The accelerometer unit of claim 7 further comprising fast recovery means for preventing said electrical signal from affecting the continuing operation of the amplification circuit subsequent to an overload condition of the piezoelectric transducer.

9. The accelerometer unit of claim 8 wherein the fast recovery means comprises a second amplification circuit and a band pass filter connected to an output of the first amplification circuit.

* * * * *